Jan. 28, 1958 E. S. BOERNER Plant Pat. 1,676
CHRYSANTHEMUM PLANT
Filed May 16, 1957
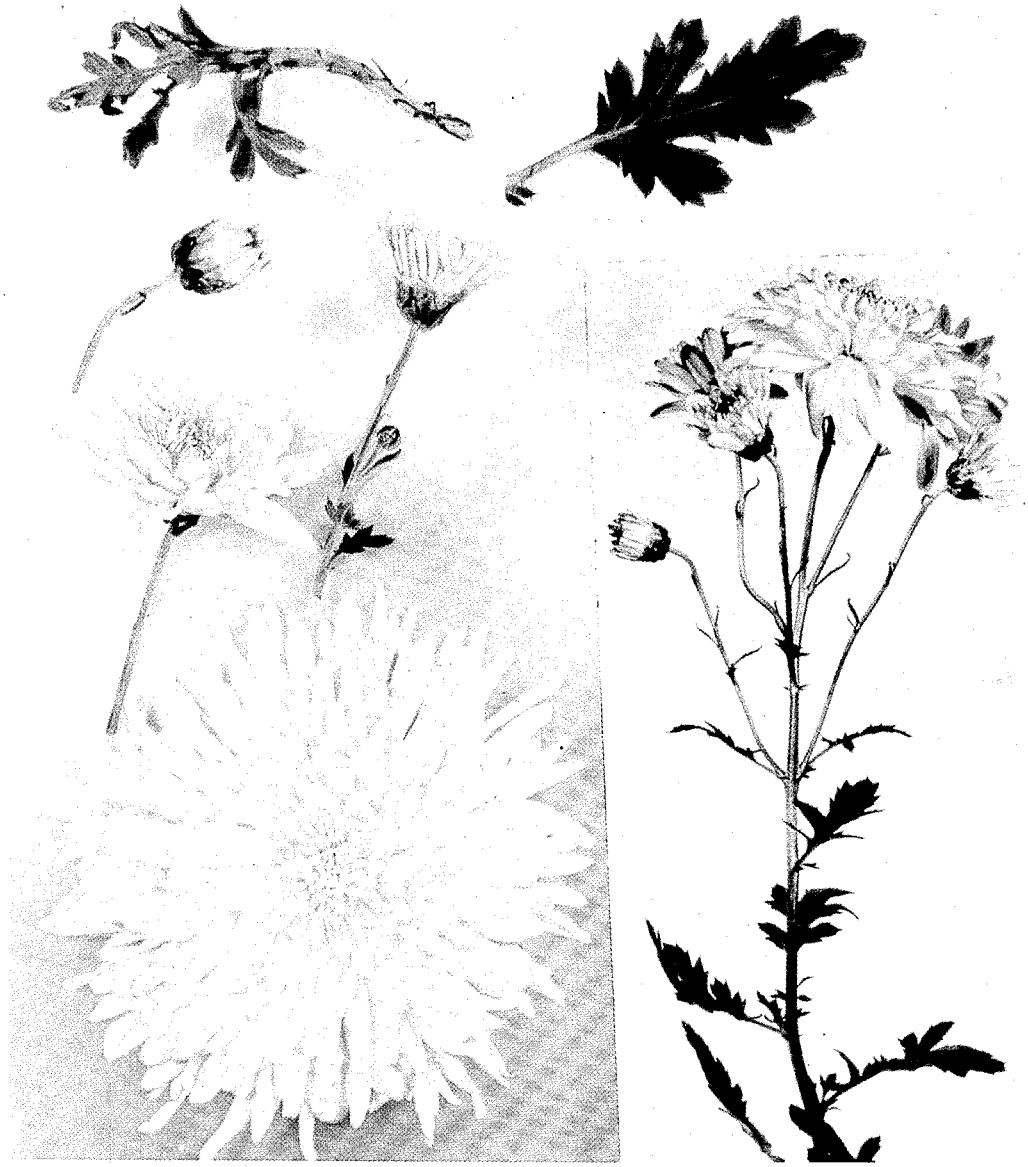
Inventor.
E. S. Boerner
By: Robb & Robb
Attorneys.

United States Patent Office

Plant Pat. 1,676
Patented Jan. 28, 1958

1,676

CHRYSANTHEMUM PLANT

Eugene S. Boerner, Newark, N. Y., assignor to Jackson & Perkins Company, Newark, N. Y., a corporation of New York Application May 16, 1957, Serial No. 659,739

1 Claim. (Cl. 47—60)

The present invention relates to a new and distinct variety of chrysanthemum plant of the decorative type, which was originated by me by crossing an unnamed and unpatented seedling derived from a cross of "Thrush" (Plant Patent No. 1,168) × "Seagull" (Plant Patent No. 1,130) with the variety "Yellow Seagull" (Plant Patent No. 1,547).

The primary objective of this breeding was to produce a new chrysanthemum variety which bears flowers of a new color, while simultaneously retaining the large flower size of the parent variety "Yellow Seagull," and the plant vigor of the variety "Thrush." This objective was fully achieved, along with other improved features, as evidenced by the following characteristics which are outstanding in the new variety and which represent a unique combination in a chrysanthemum of this class:

(1) A compact and bushy habit of growth;

(2) A vigorous plant growth corresponding to that of the variety "Thrush";

(3) A prolific flower production;

(4) A large flower size; and (5) A distinctive Orange-Buff general color tonality of the flowers which is a new color in the chrysanthemum world.

The foregoing characteristics and distinctions definitely differentiate the new variety from its parents, as well as from all other varieties of its class of which I am aware, and asexual reproduction of the new variety by both top cuttings and underground runners, as performed at Newark, New York, shows that these characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character, as well as a typical specimen plant which is depicted in black-and-white, as illustrative of the form and habit of growth of the plant.

The following is a detailed description of my new variety, with color terminology in accordance with Ridgway's Color Standards and Nomenclature, as based upon observations made from specimens grown outdoors at Newark, New York, in the nearly afternoon during the latter part of the month of September:

Parentage: An unnamed yellow seedling derived from a cross of "Thrush" × "Seagull" × "Yellow Seagull."

Classification: Decorative.

Growth: Upright; attains a height averaging about 24 inches.

Cold Resistance: Plants are very winter hardy in northern New York, but flowers show a slight frost burn from early frosts.

Blooming Period: In the Newark, New York climatic area, blooming begins about September 15th, with blooms continuing very prolifically until heavy frosts.

*Flower*

Bud:

*Color.*—When sepals first divide — Orange-Buff, Plate 3. When petals begin to unfurl—Orange-Buff, Plate 3, lightened with Antimony Yellow, Plate 15. When half-blown: inside of petals—Capucine Orange, Plate 3; reverse of petals—Light Orange-Yellow, Plate 3.

*Peduncle.*—Strong. Color—Light Grape Green, Plate 41.

Bloom:

*Size.*—Average about 4½ inches.

*Stem.*—Strong.

*Form.*—Decorative.

*Petalage.*—Double.

*Color.*—Center of flower—Orange-Buff, Plate 3. Outer petals—Pale Orange-Yellow, Plate 3. Base of petals—Pale Greenish Yellow, Plate 5. Inside of petals—Orange-Buff, Plate 3, faintly overcast with Pale Yellow-Orange, Plate 3. Reverse of petals—Baryta Yellow, Plate 4.

*Petals.*—Texture—stiff. Form—pointed.

*Fragrance.*—Characteristic chrysanthemum.

*Plant*

Form: Compact; bushy.

Growth: Free.

Foliage:

*Size.*—Medium.

*Quantity.*—Normal.

*Color.*—Upper side—Yew Green, Plate 31. Reverse side—Light Hellebore Green, Plate 17.

*Texture.*—Leathery.

I claim:

A new and distinct variety of chrysanthemum plant of the decorative type, substantially as herein shown and described, characterized particularly as to novelty by its vigorous, compact and bushy habits of plant growth, its floriferousness, the large size of its flowers, and the distinctive Orange-Buff general color tonality of its flowers.

No references cited.